United States Patent [19]

Welter et al.

[11] Patent Number: 5,155,136
[45] Date of Patent: Oct. 13, 1992

[54] FUNGICIDAL, 2-ACYLACETANILIDE DERIVATIVES

[75] Inventors: Thomas R. Welter, Webster; John J. Delany, III, Rochester, both of N.Y.

[73] Assignee: Eastman Kodak Company, Rochester, N.Y.

[21] Appl. No.: 617,242

[22] Filed: Nov. 23, 1990

[51] Int. Cl.$^5$ ............................................. A01N 41/06
[52] U.S. Cl. .................... 514/604; 514/603; 564/86
[58] Field of Search ............... 514/604, 625, 628, 603; 564/199, 86

[56] References Cited

U.S. PATENT DOCUMENTS

| | | | |
|---|---|---|---|
| 3,061,643 | 10/1962 | Pawloski | 260/562 |
| 4,130,662 | 12/1978 | Pallos | 424/324 |
| 4,304,845 | 12/1981 | Fujimatsu et al. | 430/389 |
| 4,427,696 | 1/1984 | Hubele | 424/309 |

FOREIGN PATENT DOCUMENTS

| | | |
|---|---|---|
| 0001650 | 2/1978 | European Pat. Off. . |
| 100139 | 7/1971 | Fed. Rep. of Germany . |
| 76589 | 7/1973 | Japan . |
| 8803132 | 5/1988 | PCT Int'l Appl. . |

OTHER PUBLICATIONS

Japanese Patents Gazette, Section CH, Week 7538, 28 Oct. 1975, Class C, Page 1, AN 75-62983W/38 *abstract* & JP-A-50 024 441 15 Mar. 1975.

Collection of Czechoslovak Chem. Comm., V. 44, No. 5 1979, pp. 1560–1567, J. Korinek et al.

Patent Abstracts of Japan, v. 5, No. 8; 20 Jan. 1981 & JP-A-55 136 204, 23 Oct. 1980.

Primary Examiner—Allen J. Robinson
Assistant Examiner—John D. Pak
Attorney, Agent, or Firm—B. J. Deaton

[57] ABSTRACT

A method of controlling fungus is provided which comprises contacting said fungus with a fungicidally effective amount of a compound having the following structure:

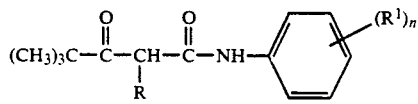

wherein
R is a halogen atoem, and
R$^1$ is selected from the group consisting of substituted or unsubstituted, straight or branched alkyl having from about 1 to 6 carbon atoms, alkoxy having from about 1 to 6 carbon atoms, halo, provided that when any R$^1$ is chloro, n is 2 and at least one R$^1$ is meta-chloro, substituted or unsubstituted sulfamoyl, and substituted or unsubstituted carbamoyl,
where n is 1 or 2.

4 Claims, No Drawings

5,155,136

FUNGICIDAL, 2-ACYLACETANILIDE DERIVATIVES

FIELD OF THE INVENTION

The present invention relates to fungicides.

BACKGROUND OF THE INVENTION

There is a continual need in the food agricultural industry for a variety of fungicidal methods which are useful to the public. The fungicidal method of this invention utilizes compounds which are derivatives of 2-acylacetanilide.

There are various anilides which are useful in fungicidal methods. In U.S. Pat. No. 4,427,696, entitled "Fungicidal Acyl Anilides", assigned to Ciba-Geigy Corp., dated Jan. 24, 1984, acyl anilides useful as microbicides are disclosed. They are preferably used for combating phytopathogenic fungi.

Collection Czechoslov. Chem. Commun., Vol. 44, pages 1460–1467 (1979), discloses derivatives of pivaloylacetanilide which are used as couplers and which are chromogenously developed in the preparation of azomethine dyestuffs in gelatin layer.

PCT application C07C 103/375, A01N 37/42, Priority date Oct. 28, 1986, published May 5, 1988, by the Dow Chemical Company, Midland, MI, entitled "Fungicidal 4-monohalogenacetoacetanilide" discloses 4-monohalogenacetacetanilides having a fungicidal use.

Other compounds which appear to be similar to the compounds of the invention are found in Japanese Application Number 76589/73 dated Jul. 9, 1973, Laid-Open Number 24441/75, Laid-Open Date: Mar. 15, 1975, by Permachem Asia, entitled "Sterile Composition" which discloses a sterile composition for nonmedical use comprising as an active ingredient a compound represented by general formula:

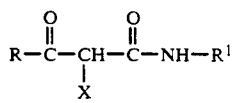

wherein X represents a halogen atom or a thiocyano group; R represents an alkyl group or a phenyl group; and $R^1$ represents a hydrogen atom, an alkyl group or an aryl group. This publication teaches the use of compounds of the above formula as agents for preventing slime or moulds in paper making steps, antimould agents of pulp, antiseptic and antimould agents for paints, oils for treating fibers, antiseptics, bacteriocides for seeds in agricultural use, etc. Particularly, Example 2 discloses α-iodoacetoacetanilide being mixed with wheat starch in a concentration of 0.02%. This mixture was allowed to stand in an incubator at 35 (°C.) for a month. To the contrary, where no chemical was added, mould generated 3 days after and 7 days after, so that the whole surface was covered with mould. This publication does not disclose testing of the compounds for fungicidal activity on a broad range of phytopathogenic fungi. Therefore, it is not known that these compounds exhibit any fungicidal activity on any fungus other than that found in wheat starch.

SUMMARY OF THE INVENTION

We have discovered a novel fungicidal method which provides an alternative to existing fungicidal methods.

More specifically, in accordance with the present invention, there is provided a method of controlling fungus which comprises contacting said fungus with a fungicidally effective amount of a compound having the following structure:

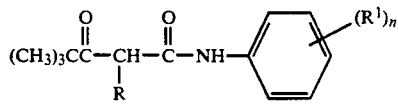

wherein
R is a halogen atom, and
$R^1$ is selected from the group consisting of substituted or unsubstituted, straight or branched alkyl having from about 1 to 6 carbon atoms, alkoxy having from about 1 to 6 carbon atoms, halo, provided that when any $R^1$ is chloro, n is 2 and at least one $R^1$ is meta-chloro, substituted or unsubstituted sulfamoyl, and substituted or unsubstituted carbamoyl, where n is 1 or 2.

It is an advantageous feature of the invention that it provides a fungicidal method which is an alternative to existing fungicidal methods.

It is also an advantageous feature of the invention that it provides excellent fungicidal activity against at least two different classes of fungi.

DESCRIPTION OF THE PREFERRED EMBODIMENTS

The invention provides a method of controlling fungus which comprises contacting said fungus with a fungicidally effective amount of a compound having the structure:

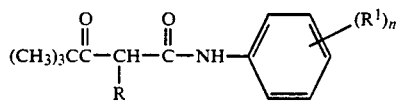

wherein
R is a halogen atom, such as bromo, chloro, fluoro, and iodo; and
$R^1$ is selected from the group consisting of substituted or unsubstituted, straight or branched alkyl having from about 1 to 6 carbon atoms, for example, trifluoromethyl, perfluoroethyl, methyl, ethyl, propyl, isopropyl, butyl, isobutyl, tertiary butyl, pentyl, hexyl, benzyl, phenethyl, substituted hydroxypropyl, dihydroxypropyl and chlorobutyl,
alkoxy having from about 1 to 6 carbon atoms, for example, methoxy, propoxy, isopropoxy, and butoxy, isobutoxy, pentoxy, and hexyloxy,
halo, for example, chloro, fluoro, bromo, and iodo, provided that when any $R^1$ is chloro, n is 2 and at least one $R^1$ is meta-chloro,
substituted or unsubstituted sulfamoyl, for example, sulfamoyl, N-methylsulfamoyl, N,N-dimethylsulfamoyl, N,N-diethylsulfamoyl, and N-butyl-N-methylsulfamoyl, and
substituted or unsubstituted carbamoyl, with suitable substituents being lower alkyl of about 1 to 6 carbon atoms for example, carbamoyl, N-methylcarbamoyl, N,N-dimethylcarbamoyl, N,N-diethylcarbamoyl, and N-butyl-N-methylcarbamoyl; and n is 1 or 2.

Preferred methods of the invention include ones utilizing the compounds having the above structure wherein $-(R^1)_n$ substituents are 3,4-dichloro, 3,5-dichloro, 4-methoxy, 4-(n-butyl-N-methylsulfamoyl), 4-methyl, 4-trifluoromethyl, 4-t-butyl, 5-chloro-2-methoxy, 4-bromo, and 4-fluoro.

Particularly preferred compounds of the invention are ones having the above structure wherein $-(R^1)_n$ substituents are 3,4-dichloro, 3,5-dichloro, and 4-trifluoromethyl.

Compounds representative of the ones useful in the method of this invention include:
2,3',4'-Trichloro-2-pivaloylacetanilide,
2-chloro-4'-methoxy-2-pivaloylacetanilide,
2-chloro-4'-N-methyl-N-butylsulfamoyl-2-pivaloylacetanilide,
2-chloro-4'-methyl-2-pivaloylacetanilide,
2,3',5'-trichloro-2-pivaloylacetanilide,
2-chloro-2-pivaloyl-4'-trifluoromethylacetanilide,
2,5'-dichloro-2'-methoxy-2-pivaloylacetanilide,
4'-bromo-2-chloro-2-pivaloylacetanilide,
2-chloro-4'-fluoro-2-pivaloylacetanilide, and
4'-t-butyl-2-chloro-2-pivaloylacetanilide.

Further, a fungicidal composition is provided comprising a fungicidally effective amount of at least one of the above compounds useful in the method of the invention as an active ingredient.

The present invention provides a means for controlling *Colletotrichum graminicola* (Anthracnose on corn), *Alternaria solani* (Early blight on tomatoes), *Botrytis cinerea* (gray mold on peppers), *Phytophthora infestans* (late blight on tomatoes), *Erysiphe graminis* f.sp. tritici (Powdery mildew on wheat), and *Puccinia recondita* f. sp. tritici (Wheat leaf rust), and other fungi. The compounds of the invention showed particularly enhanced activity on at least two of the above fungi.

The 2-acylacetanilide derivatives are generally obtainable as colorless to yellow crystalline materials having characteristic melting points and absorption spectra and which may be purified by recrystallization from common organic solvents. They are appreciably soluble in many organic solvents such as methanol, ethanol, acetone, chloroform, benzene, dioxane, dimethyl sulfoxide and N,N-dimethylformamide, but are relatively insoluble in water. The 2-acylacetanilide derivatives used in the invention can be applied as fungicidal sprays by methods commonly employed at varying concentrations, air-blast, aerial sprays and dusts. The dilution and rate of application will depend upon the type of equipment employed, the method and frequency of application desired and diseases to be controlled.

The compounds of the invention can be prepared in general through minor modifications of literature procedures. The preparations of certain 1-Pivaloylacetanilide derivatives are generally described in *Collection Czechoslov. Chem. Commun.*, Vol. 44, pages 1460–1467 (1979), by Korinek et al. This reference gives examples of the preparation of derivatives of 1-Pivaloylacetanilide, 1-Chloro-1-pivaloylacetanilide, 1-Acetoxy-1-pivaloylacetanilide, and azomethine dye stuffs.

The 2-acylacetanilides used in the invention can be applied as fungicidal sprays by methods commonly employed at varying concentrations, including air-blast, aerial sprays and dusts. The dilution and rate of application will depend upon the type of equipment employed, the method and frequency of application desired and diseases to be controlled.

Such active compounds may be employed alone or in the form of mixtures with such solid and/or liquid carrier vehicles and/or with other known compatible active agents, especially plant protection agents, such as other insecticides, nematocides, or acaricides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

The process of the present invention is useful for the control of various fungi as described herein, and can be utilized on the foliage. For such purposes, these compounds can be used in solutions, liquid formulations, or dry powder formulations. The compounds are usually taken up in a carrier or are formulated so as to render them suitable for subsequent use as fungicides. For example, these chemical agents can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Some adjuvants commonly used in the art can be found in McCutcheon's Emulsifiers and Detergents/Functional Materials and McCutcheon's Functional Materials all published annually by McCutcheon Division of MC Publishing Company (New Jersey).

In general, the compounds utilized in this invention can be dissolved in appropriate solvents such as acetone, methanol, ethanol, dimethylformamide, or methyl sulfoxide and such solutions extended with water. The concentration of the solution can vary from 1 to 90% with a preferred range being (5 to 50%).

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10 to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations varies widely.

Dusts are prepared by mixing the 2-acylacetanilides with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrations containing 20% to 80% of the active ingredient are commonly made and are subsequently diluted to 1% to 10% use concentration.

EXAMPLE I

The compounds used in this invention were evaluated as protectant fungicides by a standard method as follows. The results of these primary evaluations are recorded in Table II. Furthermore, these compounds were evaluated for their dose response profiles against the pathogens as shown in Table I.

Plant Disease Control Assay Primary Screening for Fungicidal Activity (Protectant)

Tomatoes, peppers, beans and corn are germinated and grown for one to three weeks (depending on species) in the greenhouse. Two pots representing two replicates of each plant species are placed in a flat such that each flat contains all the plants to be sprayed by one compound. The plants in each flat are sprayed to runoff at the rate of 135 ppm with either a test compound or fungicide standard. As a control, check plants are sprayed with water. The plants are allowed to air dry two to three hours. After drying, the plants are sorted and grouped by plant species.

Plant pathogenic fungi (*Phytophthora infestans, Alternaria solani, Botrytis cinerea, Colletotrichum graminicola*) are grown in the laboratory on appropriate media. Inoculum from each fungus is harvested and concentrations adjusted to predetermined levels. The obligate plant pathogenic fungi (*Erysiphe graminis* f.sp. tritici, *Puccinia recondita* f.sp. tritici) are harvested from their hosts in the greenhouse and concentrations are adjusted to predetermined levels.

The plants previously treated with test compounds are sprayed with fungal inoculum and then placed in humidity chambers for a period of time previously determined to be optimum for development of each disease. After incubation, the plants are moved to the greenhouse, symptoms allowed to develop (one week), and the plants evaluated for disease intensity. The reported percent disease control represents the average of the two replicates.

Secondary Screening for Fungicidal Activity (Protectant, Systemic)

Compounds providing a minimum of 75% disease control for at least two diseases or compounds demonstrating efficacy greater than 90% for a single disease are automatically advanced to secondary screening.

Fungicidal efficacy is titrated to the no effect level on the diseases controlled in the primary screen. Plants are grown and prepared for spraying as in the primary screen except that three replicates are used. The test compounds or fungicide standards are sprayed to runoff at concentrations of 5, 15, 45 and 135 ppm. As a control, check plants are sprayed with water. The plants are allowed to air-dry and then fungal inoculum is applied as in the primary screen. In addition to the protectant spray test, a soil drench application is included in the secondary screen to detect root uptake and systemic activity. Plants are grown and prepared as in the primary screen. The soil of each pot is drenched with 25 ml of either a test compound or fungicide standard at a concentration of 135 ppm. Each treatment is replicated three times. The plants are allowed to stand 4–5 hours before spraying with the fungal inoculum.

The inoculated plants from the protectant spray and soil drench studies are incubated in humidity chambers, moved to the greenhouse for symptom development, then rated for disease. The reported percent disease control in Table II represents the average of three replicates.

TABLE I

| | Pathogens | | |
|---|---|---|---|
| Common Name | Scientific Name | Host | Abbr. |
| Anthracnose | *Colletotrichum graminicola* | Corn | MA |
| Early blight | *Alternaria solani* | Tomato | EB |
| Gray mold | *Botrytis cinerea* | Pepper | BC |
| Late blight | *Phytophthora infestans* | Tomato | LB |
| Powdery mildew | *Erysiphe graminis* f. sp. tritici | Wheat | WM |
| Rust | *Puccinia recondita* f. sp. tritici | Wheat | WR |

TABLE II

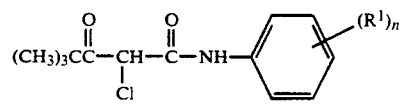

| | | PERCENT CONTROL | | | | | |
|---|---|---|---|---|---|---|---|
| | (R¹)N | LB | EB | BC | MA | WR | WM |
| PART A COMPOUNDS | | | | | | | |
| 1 | 3,4-Cl$_2$ | 60 | 0 | 0 | 95 | 0 | 50 |
| 2 | 4-OMe | 60 | 0 | 0 | 80 | 0 | 0 |
| 3 | 4-SO$_2$N(Me)Bu | 80 | 0 | 0 | 0 | 50 | 30 |
| 4 | 4-Me | 65 | 0 | 0 | 90 | 0 | 0 |
| 5 | 3,5-Cl$_2$ | 80 | 0 | 0 | 80 | 45 | 70 |
| 6 | 4-CF$_3$ | 80 | 0 | 80 | 40 | 70 | 0 |
| 7 | 2-OMe-5-Cl | 50 | 0 | 0 | 40 | 0 | 0 |
| 8 | 4-Br | 50 | 0 | 70 | 85 | 0 | 0 |
| 9 | 4-F | 20 | 30 | 60 | 70 | 0 | 0 |
| 10 | 4-tBu | 60 | 0 | 0 | 90 | 60 | 0 |
| PART B CONTROLS | | | | | | | |
| 1 | 4-Cl | 50 | 0 | 0 | 20 | 0 | 0 |
| 2 | 2,4-Cl$_2$ | 0 | 0 | 0 | 0 | 60 | 0 |
| 3 | 2-Cl | 0 | 0 | 0 | 50 | 50 | 0 |
| 4 | 2-F | 0 | 0 | 0 | 0 | 0 | 0 |
| 5 | 2-OMe | 0 | 0 | 0 | 0 | 0 | 0 |
| 6 | 2-Me | 0 | 0 | 0 | 0 | 0 | 0 |
| 7 | 2-Et | 0 | 0 | 0 | 0 | 0 | 0 |

TABLE II-continued

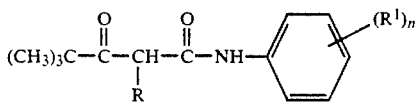

|  | $(R^1)N$ | PERCENT CONTROL ||||||
|---|---|---|---|---|---|---|---|
|  |  | LB | EB | BC | MA | WR | WM |
| 8 | 2,5-$Cl_2$ | 0 | 0 | 0 | 0 | 0 | 0 |
| 9 | 2,4,5-$Cl_3$ | 0 | 0 | 0 | 0 | 0 | 0 |
| 10 | 3-$CF_3$ | 0 | 0 | 0 | 0 | 0 | 0 |
| 11 | 2-$CF_3$ | 0 | 0 | 0 | 0 | 0 | 0 |

The invention has been described in detail with particular reference to certain preferred embodiments thereof, but it will be understood that variations and modifications can be effected within the spirit and scope of the invention.

What is claimed is:

1. A method of controlling fungus which comprises contacting said fungus with a fungicidally effective amount of a compound having the structure

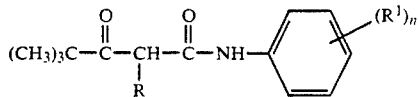

wherein
R is a halogen atom, and
$R^1$ is substituted or unsubstituted sulfamoyl, wherein said substituents are selected from methyl, ethyl and butyl,
where n is 1 or 2.

2. The method according to claim 1 wherein $R^1$ is $SO_2N(Me)Bu$ and n is 1.

3. A fungicidal composition which contains a carrier, and, as an active ingredient, a fungicidally effective amount of a compound having the structure:

$$(CH_3)_3C-\overset{O}{\underset{}{C}}-\underset{R}{\overset{}{CH}}-\overset{O}{\underset{}{C}}-NH-\underset{}{\underset{}{\bigcirc}}-(R^1)_n$$

wherein
R is a halogen atom, and
$R^1$ is substituted or unsubstituted sulfamoyl, wherein said substituents are selected from methyl, ethyl and butyl,
where n is 1 or 2.

4. A fungicidal composition comprising a fungicidally effective amount of 2-chloro-4'-N-methyl-N-butylsulfamoyl-2-pivaloylacetanilide.

* * * * *